(12) United States Patent
Farley et al.

(10) Patent No.: US 9,693,898 B2
(45) Date of Patent: Jul. 4, 2017

(54) DOUBLE-ACTING VITREOUS PROBE WITH CONTOURED PORT

(71) Applicant: Novartis AG, Basel (CH)

(72) Inventors: Mark Farley, Laguna Hills, CA (US); Brian William McDonell, Irvine, CA (US)

(73) Assignee: Novartis AG, Basel (CH)

( * ) Notice: Subject to any disclaimer, the term of this patent is extended or adjusted under 35 U.S.C. 154(b) by 77 days.

(21) Appl. No.: 14/547,250

(22) Filed: Nov. 19, 2014

(65) Prior Publication Data

US 2016/0135991 A1    May 19, 2016

(51) Int. Cl.
*A61B 17/32*    (2006.01)
*A61F 9/007*    (2006.01)

(52) U.S. Cl.
CPC .... *A61F 9/00763* (2013.01); *A61B 2218/007* (2013.01)

(58) Field of Classification Search
CPC ............. A61F 9/00763; A61F 9/00736; A61B 2017/00544; A61B 17/320783; A61B 10/0266; A61B 10/0275; A61B 10/0283; A61B 17/32; A61B 17/32002; A61B 2017/320028; A61B 2217/005; A61B 2218/007
USPC .......... 606/166, 169, 170, 171, 180; 604/22; 600/562, 564, 566, 567
See application file for complete search history.

(56) References Cited

U.S. PATENT DOCUMENTS

| 3,618,594 | A | 11/1971 | Banko |
| 3,736,938 | A | 6/1973 | Evvard et al. |
| 3,815,604 | A | 6/1974 | O'Malley et al. |
| 3,906,954 | A | 9/1975 | Baehr et al. |
| 3,941,122 | A | 3/1976 | Jones |
| 3,982,541 | A | 9/1976 | L'Esperance, Jr. |
| 4,011,869 | A | 3/1977 | Seiler, Jr. |
| 4,014,342 | A | 3/1977 | Staub et al. |

(Continued)

FOREIGN PATENT DOCUMENTS

| CH | 704384 A2 | 7/2012 |
| DE | 20022265 U1 | 6/2001 |

(Continued)

OTHER PUBLICATIONS

International Searching Authority, International Search Report, PCT/US2015/056572, Apr. 12, 2016, 8 pages.

(Continued)

*Primary Examiner* — Katherine M Shi

(57) ABSTRACT

A vitrectomy probe includes a hand-graspable body and an outer tube extending from the hand-graspable body. The outer tube includes a closed distal end and a first port sized to receive tissue. The vitrectomy probe also includes an inner tube within the outer tube with a second port that is selectively alignable with a portion of the first port to allow fluid flow and uniquely sized to increase fluid flow. The inner tube includes a distal tip with a cutting edge on each of the distal and proximal sides of the tip. The distal tip has a smaller diameter than that of the inner tube at a proximal side of the second port. The proximal side of the second port includes a guiding surface that slidably bears on an inner surface of the outer tube to prevent the distal tip from excessively protruding from the first port of the outer tube.

13 Claims, 9 Drawing Sheets

(56) References Cited

U.S. PATENT DOCUMENTS

| | | |
|---|---|---|
| 4,099,529 A | 7/1978 | Peyman |
| 4,111,207 A | 9/1978 | Seiler, Jr. |
| 4,210,146 A | 7/1980 | Banko |
| 4,428,748 A | 1/1984 | Peyman et al. |
| 4,513,745 A | 4/1985 | Amoils |
| 4,525,842 A | 6/1985 | Myers |
| 4,577,629 A | 3/1986 | Martinez |
| 4,583,539 A | 4/1986 | Karlin et al. |
| 4,655,743 A | 4/1987 | Hyde |
| 4,671,273 A | 6/1987 | Lindsey |
| 4,694,828 A | 9/1987 | Eichenbaum |
| 4,696,298 A | 9/1987 | Higgins et al. |
| 4,811,734 A | 3/1989 | McGurk-Burleson et al. |
| 4,846,172 A | 7/1989 | Berlin |
| 4,909,249 A | 3/1990 | Akkas et al. |
| 4,940,468 A | 7/1990 | Petillo |
| 4,963,142 A | 10/1990 | Loertscher |
| 5,019,035 A | 5/1991 | Missirlian et al. |
| 5,047,008 A | 9/1991 | de Juan, Jr. et al. |
| 5,106,364 A | 4/1992 | Hayafuji et al. |
| 5,176,628 A | 1/1993 | Charles et al. |
| 5,226,910 A | 7/1993 | Kajiyama |
| 5,275,607 A | 1/1994 | Lo et al. |
| 5,284,472 A | 2/1994 | Sussman et al. |
| 5,285,795 A | 2/1994 | Ryan et al. |
| 5,423,844 A | 6/1995 | Miller |
| 5,458,112 A | 10/1995 | Weaver |
| 5,474,532 A | 12/1995 | Steppe |
| 5,547,473 A | 8/1996 | Peyman |
| 5,630,827 A | 5/1997 | Vijfvinkel |
| 5,688,264 A | 11/1997 | Ren et al. |
| 5,720,760 A | 2/1998 | Becker et al. |
| 5,772,627 A | 6/1998 | Acosta et al. |
| 5,782,849 A | 7/1998 | Miller |
| 5,788,667 A | 8/1998 | Stoller |
| 5,843,111 A | 12/1998 | Vijfvinkel |
| 5,980,546 A | 11/1999 | Hood |
| 5,984,916 A | 11/1999 | Lai |
| 6,004,284 A | 12/1999 | Sussman et al. |
| 6,024,751 A | 2/2000 | Lovato et al. |
| 6,027,493 A | 2/2000 | Donitzky et al. |
| 6,156,049 A | 12/2000 | Lovato et al. |
| 6,258,111 B1 | 7/2001 | Ross et al. |
| 6,270,471 B1 | 8/2001 | Hechel et al. |
| 6,325,792 B1 | 12/2001 | Swinger et al. |
| 6,352,535 B1 | 3/2002 | Lewis et al. |
| 6,383,203 B1 | 5/2002 | Makihara |
| 6,485,499 B1 | 11/2002 | Oberkamp et al. |
| 6,514,268 B2 | 2/2003 | Finlay et al. |
| 6,575,990 B1 | 6/2003 | Wang et al. |
| 6,709,408 B2 | 3/2004 | Fisher |
| 6,743,245 B2 | 6/2004 | Lobdell |
| 6,758,824 B1 | 7/2004 | Miller et al. |
| 6,773,445 B2 | 8/2004 | Finlay et al. |
| 6,872,185 B2 | 3/2005 | Fisher |
| 6,875,221 B2 | 4/2005 | Cull |
| 6,890,309 B2 | 5/2005 | Fisher |
| 6,908,440 B2 | 6/2005 | Fisher |
| 7,070,604 B1 | 7/2006 | Garito et al. |
| 7,285,107 B1 | 10/2007 | Charles |
| 7,600,405 B2 | 10/2009 | Maurer, Jr. et al. |
| 8,038,692 B2 | 10/2011 | Valencia et al. |
| 8,172,865 B2 | 5/2012 | DeBoer et al. |
| 8,187,293 B2 | 5/2012 | Kirchhevel |
| 8,298,253 B2 | 10/2012 | Charles |
| 8,313,501 B2 | 11/2012 | Miller et al. |
| 8,328,835 B2 | 12/2012 | Perkins et al. |
| 8,545,528 B2 | 10/2013 | Rob et al. |
| 8,608,753 B2 | 12/2013 | Luloh et al. |
| 8,641,701 B2 | 2/2014 | Hangai et al. |
| 8,728,108 B2 | 5/2014 | Gao et al. |
| 8,808,318 B2 | 8/2014 | Auld et al. |
| 8,818,564 B2 | 8/2014 | Zhou et al. |
| 8,821,524 B2 | 9/2014 | Agahi |
| 8,979,867 B2 | 3/2015 | Peyman |
| 9,060,841 B2 | 6/2015 | McCawley |
| 9,101,442 B2 | 8/2015 | McDonell |
| 9,211,608 B2 | 12/2015 | Chen et al. |
| 9,216,067 B2 | 12/2015 | Peyman |
| 2003/0032895 A1 | 2/2003 | Fisher |
| 2003/0114870 A1 | 6/2003 | Cull |
| 2003/0195538 A1 | 10/2003 | Wang et al. |
| 2004/0049217 A1 | 3/2004 | Ross et al. |
| 2004/0133190 A1 | 7/2004 | Hobart et al. |
| 2004/0167428 A1* | 8/2004 | Quick ............... A61B 10/0275 600/564 |
| 2005/0090765 A1 | 4/2005 | Fisher |
| 2005/0154379 A1 | 7/2005 | McGowan, Sr. et al. |
| 2005/0187537 A1 | 8/2005 | Loeb et al. |
| 2005/0209618 A1 | 9/2005 | Auld |
| 2006/0004397 A1 | 1/2006 | Osawa |
| 2006/0161145 A1 | 7/2006 | Lin et al. |
| 2006/0271082 A1 | 11/2006 | Kirchhevel et al. |
| 2007/0088376 A1 | 4/2007 | Zacharias |
| 2007/0129732 A1 | 6/2007 | Zacharias |
| 2007/0173870 A2 | 7/2007 | Zacharias |
| 2007/0185514 A1 | 8/2007 | Kirchhevel |
| 2007/0255196 A1 | 11/2007 | Wuchinich |
| 2008/0154292 A1 | 6/2008 | Huculak et al. |
| 2008/0172077 A1 | 7/2008 | Valencia et al. |
| 2008/0172078 A1 | 7/2008 | Svetic |
| 2008/0188881 A1 | 8/2008 | Chon |
| 2008/0208233 A1 | 8/2008 | Barnes et al. |
| 2009/0069831 A1 | 3/2009 | Miller et al. |
| 2009/0088784 A1 | 4/2009 | DeBoer et al. |
| 2009/0157111 A1 | 6/2009 | Goh et al. |
| 2009/0259242 A1 | 10/2009 | Gerg et al. |
| 2009/0281479 A1 | 11/2009 | Gagnepain et al. |
| 2010/0042125 A1 | 2/2010 | Maurer, Jr. et al. |
| 2010/0106054 A1 | 4/2010 | Hangai et al. |
| 2010/0152762 A1 | 6/2010 | Mark |
| 2010/0305596 A1 | 12/2010 | Peterson et al. |
| 2010/0312169 A1 | 12/2010 | Auld et al. |
| 2011/0144641 A1 | 6/2011 | Dimalanta, Jr. et al. |
| 2011/0190690 A1 | 8/2011 | Humayun et al. |
| 2011/0295292 A1 | 12/2011 | Hsia |
| 2011/0295296 A1 | 12/2011 | Charles |
| 2012/0083793 A1 | 4/2012 | Foster |
| 2012/0158030 A1 | 6/2012 | Underwood et al. |
| 2012/0221033 A1 | 8/2012 | Auld et al. |
| 2013/0053759 A1 | 2/2013 | McCawley |
| 2013/0090635 A1 | 4/2013 | Mansour |
| 2013/0110147 A1 | 5/2013 | Dame |
| 2013/0150875 A1 | 6/2013 | McDonell et al. |
| 2013/0211439 A1 | 8/2013 | Geuder |
| 2013/0325044 A1 | 12/2013 | Wang et al. |
| 2014/0074013 A1 | 3/2014 | McCary et al. |
| 2014/0171994 A1 | 6/2014 | Lee et al. |
| 2014/0171995 A1 | 6/2014 | McDonell |
| 2014/0171996 A1 | 6/2014 | McDonell et al. |
| 2014/0171997 A1 | 6/2014 | Nissan et al. |
| 2014/0296900 A1 | 10/2014 | Barnes et al. |
| 2014/0364885 A1 | 12/2014 | Wells et al. |
| 2015/0157503 A1 | 6/2015 | Chon |
| 2015/0182379 A1 | 7/2015 | Fantoni et al. |
| 2015/0282987 A1 | 10/2015 | McDonell |
| 2015/0306286 A1 | 10/2015 | Ross et al. |
| 2015/0335485 A1 | 11/2015 | Rieger et al. |
| 2015/0342678 A1 | 12/2015 | Deladurantaye et al. |
| 2016/0022489 A1 | 1/2016 | Hartstra |
| 2016/0120697 A1 | 5/2016 | Farley |
| 2016/0128870 A1 | 5/2016 | Mcdonell |
| 2016/0135991 A1 | 5/2016 | Farley et al. |

FOREIGN PATENT DOCUMENTS

| | | |
|---|---|---|
| DE | 10032007 A1 | 1/2002 |
| DE | 102010050337 A1 | 5/2012 |
| DE | 202013012000 U1 | 2/2015 |
| DE | 102013201784 B4 | 5/2015 |
| EP | 0919210 A1 | 6/1999 |
| EP | 2913034 A1 | 9/2015 |
| GB | 2004754 A | 4/1979 |
| GB | 2167305 B | 11/1988 |

(56) References Cited

FOREIGN PATENT DOCUMENTS

| NL | 1034654 C2 | 5/2009 |
|---|---|---|
| WO | 9409711 A1 | 5/1994 |
| WO | 9409849 A1 | 5/1994 |
| WO | 9846147 A1 | 10/1998 |
| WO | 9852502 A1 | 11/1998 |
| WO | 0047116 A1 | 8/2000 |
| WO | 0078371 A1 | 12/2000 |
| WO | 0130281 A1 | 5/2001 |
| WO | 2004026142 A1 | 4/2004 |
| WO | 2010096139 A2 | 8/2010 |
| WO | 2012059092 A1 | 5/2012 |
| WO | 2012083402 A1 | 6/2012 |
| WO | 2012125674 A1 | 9/2012 |
| WO | 2013/009576 A1 | 1/2013 |
| WO | 2013019859 A1 | 2/2013 |
| WO | 2013043455 A1 | 3/2013 |
| WO | 2013180718 A1 | 12/2013 |
| WO | 2014/002040 A1 | 1/2014 |
| WO | 2014117774 A1 | 8/2014 |
| WO | 2014142663 A1 | 9/2014 |
| WO | 2015143308 A1 | 9/2015 |
| WO | 2015158438 A1 | 10/2015 |
| WO | 2016/081133 A1 | 5/2016 |

OTHER PUBLICATIONS

International Searching Authority, Written Opinion of the International Searching Authority, PCT/US2015/056572, Apr. 12, 2016, 7 pages.
"A New Vitreous Cutter Blade Engineered for Constant Flow Vitrectomy" Retina, The Journal of Retinal and Vitreous Diseases 2014, vol. 34, No. 7 (5 pages).
"Eva, A State-of-the-Art Surgical System for Phaco-Vitrectomy" Retina Today Supplement, 2013 (16 pages).
https://web.archive.org/web/20131029212228/http://www.geuder.com/Mach2vitreouscutter, Website archive dated Oct. 29, 2013, archive site accessed on Jul. 5, 2016 (2 pages).
Rizzo, Stanislao "Performance of a Modified Vitrectomy Probe in Small-gauge Vitrectomy" Retina Today Sep. 2011 (3 pages).
Taking VR Surgery to the Next Generation, New Instruments 2013/2014, DORC brochure (6 pages).

* cited by examiner

DOUBLE-ACTING VITREOUS PROBE WITH CONTOURED PORT

BACKGROUND

The present disclosure pertains to vitrectomy probes, systems, and methods. More particularly, but not by way of limitation, the present disclosure pertains to vitrectomy probes, systems, and methods utilizing an ovalized tubular cross section and a fluid port contour providing enhanced fluid flow and a guiding surface.

Microsurgical procedures frequently require precision cutting and/or removing of various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

Microsurgical cutting probes used in posterior segment ophthalmic surgery may include a hollow outer cutting member, a hollow inner cutting member arranged coaxially with and movably disposed within the hollow outer cutting member, a port extending radially through the outer cutting member near the distal end of the outer cutting member, and a port extending radially through the inner cutting member near the distal end of the inner cutting member. Vitreous humor and/or membranes are aspirated into the open port of the outer cutting member and the inner member is actuated to distally extend the inner cutting member. As the inner cutting member extends distally, cutting surfaces on both the inner and outer cutting members cooperate to cut the vitreous and/or membranes, and the cut tissue is then aspirated away through the inner cutting member. Vitreous and/or membranes are then aspirated into the open ports of both the outer and inner cutting members and the inner member is actuated to proximally retract the inner cutting member. The inner and outer cutting members cooperate to again cut vitreous and/or membranes and aspirate the cut tissue away. The actuated extension and retraction of the inner cutting member is repeated at dynamic cycle rates between several tens to several hundred times per second.

These microsurgical cutting probes may compromise traction transmitted to the retina due, for example, to existence of an annular space existing between the outer cutting member and the inner cutting member that can cause incarceration or incomplete shearing of vitreous. In addition, vitreous and/or membranes tend to resist flow through small orifices and lumens such as those in these microsurgical cutting probes. Finally, microsurgical cutting probes' inner cutting member is typically bent near its distal end to bias the distal cutting surface toward the port in the outer cutting member, which provides a flexural side load to facilitate shearing. This can result in the inner cutting member protruding too far out of the port in the outer cutting member as the inner cutting member moves across the outer port, causing irregular high-speed dynamic shearing motion, thus increasing wear of the probe which can lead to incarceration or incomplete shearing of vitreous.

SUMMARY

In an exemplary aspect, the present disclosure is directed to a vitrectomy probe including a hand-graspable body and an outer tube extending from the hand-graspable body and sized to penetrate an eye of a patient during an ocular surgery. The outer tube may include a closed distal end and a first port sized to receive vitreous material. The vitrectomy probe also includes an inner tube disposed at least partially within the outer tube. The inner tube has a second port that is selectively alignable with a portion of the first port in a manner that allows fluid to flow through the first port and into the second port. The second port has a proximal edge and a distal edge, and the inner tube also has a distal tip that forms a first cutting edge facing in a distal direction. The distal edge of the second port forms a second cutting edge that faces in a proximal direction. The inner tube has a first diameter at the proximal end of the second port and a second diameter at the distal tip, where the first diameter is greater than the second diameter.

In an aspect, the second port of the inner tube comprises a guiding surface at the proximal edge of the second port projecting in the distal direction to form a distally extending portion. The guiding surface is arranged to slidably bear on an internal surface of the outer tube while the inner tube moves relative to the outer tube, the first diameter comprising a diameter of the inner tube at the guiding surface.

In another exemplary aspect, the second port of the inner tube comprises a first side lobe and a second side lobe each at opposite sides of the guiding surface along a circumference of the inner tube. The first and second side lobes are configured to enhance fluid flow through the second port when the guiding surface is at least partially aligned with the first port.

In another exemplary aspect, the present disclosure is directed to a vitrectomy probe including a hand-graspable body and an outer tube extending from the hand-graspable body and sized to penetrate an eye of a patient during an ocular surgery. The outer tube may include a closed distal end and a first port sized to receive vitreous material. The vitrectomy probe also includes an inner tube disposed at least partially within the outer tube. The inner tube has a second port that has a proximal end and a distal end along a side of a circumference of the inner tube near a distal end of the inner tube. The second port comprises a guiding surface at the proximal end extending in the distal direction, a first side lobe, and a second side lobe. Each of the first and second side lobes is formed in part by the guiding surface and disposed at opposite sides of the guiding surface along the circumference of the inner tube to enhance fluid flow through the second port when the guiding surface is at least partially aligned with the first port. The distally extending guiding surface is a guide for the inner tube disposed within the outer tube as the inner tube oscillates in the outer tube.

In another exemplary aspect, the present disclosure is directed to a method of operating a vitrectomy probe. The method may include axially sliding an inner tube in a distal direction within an outer tube having a first port to make a cut with a distally facing cutting edge at a distal end of a distal tip of the inner tube, the inner tube having a second port with a proximal end and a distal end. The method may also include guiding the sliding in the distal direction with a guiding surface at the proximal end of the second port, the inner tube having a first diameter at the guiding surface that is greater than a second diameter of the inner tube at the tip.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and, together with the description, serve to explain the principles of the present disclosure.

DETAILED DESCRIPTION

Figure 1:
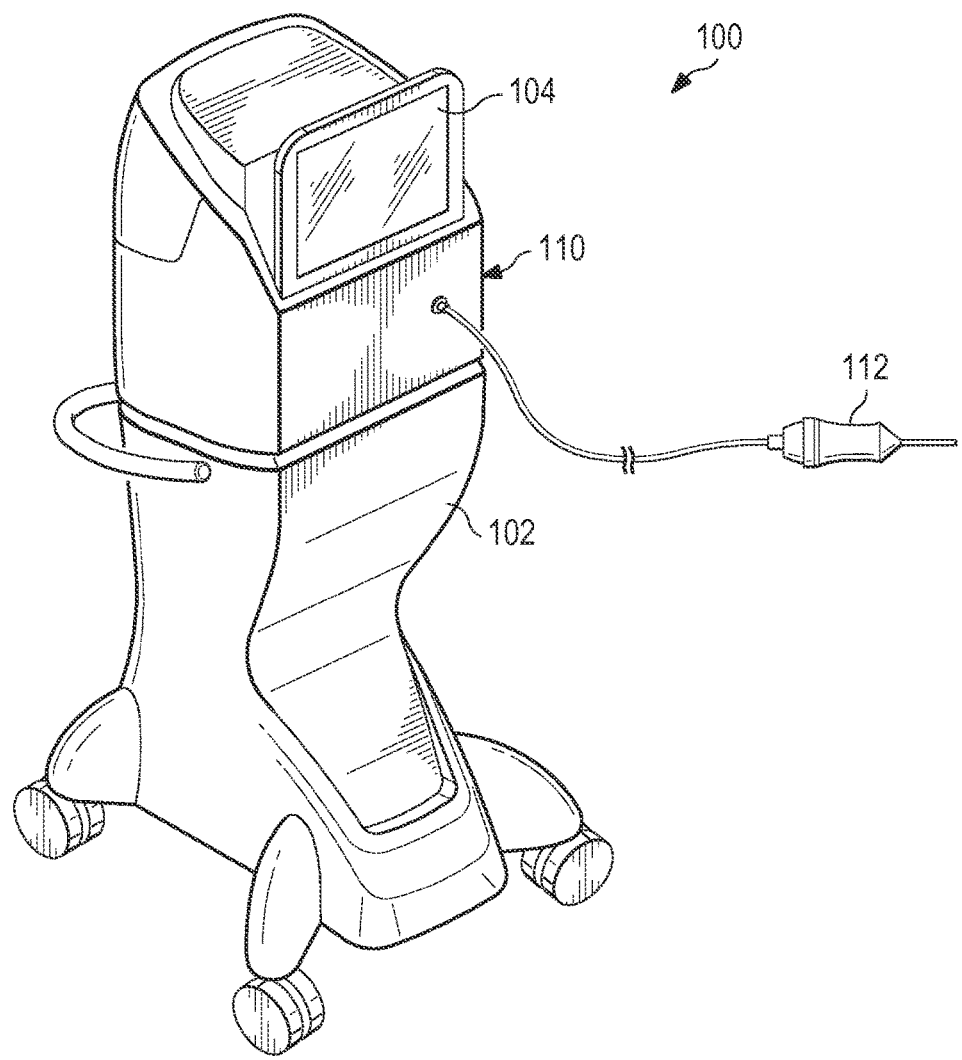
FIG. 1 is an illustration of an exemplary surgical system according to one aspect of the present disclosure consistent with the principles and teachings described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure is directed to surgical devices, systems, and methods for performing ophthalmic surgeries. The devices, systems, and methods are arranged and configured to increase a cut rate and/or an aspiration rate during a vitrectomy procedure and reduce sliding wear on the vitrectomy probe over time. To accomplish this, the system incorporates a hollow inner cutting member that includes a port with a port contour that increases vitreous flow. The port contour defines a guiding surface at a proximal end of the port in the inner cutting member, including a side lobe at each side of the guiding surface. The guiding surface defined by the port contour provides a long-wearing sliding interface between the hollow inner cutting member and a hollow outer cutting member, such as a needle. The guiding surface may slide along an inner surface of the outer cutting member, even while a portion or all of the port of the inner cutting member is aligned with the port of the outer cutting member. Increased vitreous flow is possible due to the side lobes of the inner cutting member's port. For example, the interaction of the guiding surface with the inner surface of the outer cutting member prevents the inner cutting member from protruding too far out of the port in the outer cutting member as the inner cutting member moves distally across the outer port, thus preventing irregular dynamic shearing motion and wear of the shearing edges of the inner and outer cutting members.

In addition, a tip of the inner cutting member may be imparted with a substantially oval cross section (in comparison to a circular cross-section of other portions the inner cutting member at the proximal side of the inner cutting member's port). This unique shape for the tip of the inner cutting member may provide a closer match between curvature radii of the shearing edges of the inner and outer cutting members. With a closer curvature match of the edges, smoother shearing is possible, which may reduce the amount of traction on the vitreous which is transmitted to the retina. Various aspects of these features will be discussed further below.

FIG. 1 illustrates a vitrectomy surgical system, generally designated 100, according to an exemplary embodiment. The surgical system 100 includes a base housing 102 and an associated display screen 104 showing data relating to system operation and performance during a vitrectomy surgical procedure. In an embodiment, the base housing 102 may be mobile, for example including wheels to facilitate movement as necessary. In an alternative embodiment, the base housing 102 may not include wheels. The surgical system 100 includes a vitrectomy probe system 110 that includes a vitrectomy probe 112, as will be discussed in more detail below with respect to subsequent figures.

Figure 2:
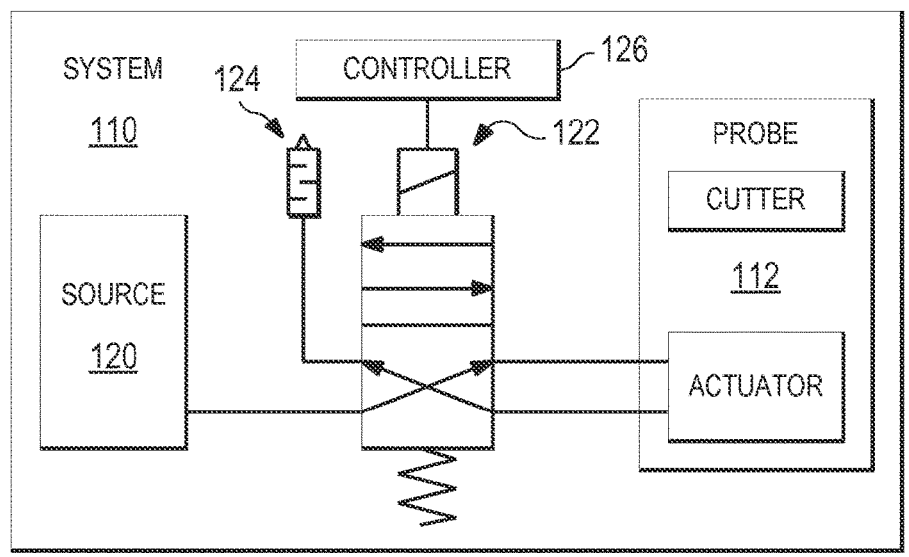
FIG. 2 is a box diagram of aspects of the exemplary surgical system of FIG. 1 according to an aspect described herein.

FIG. 2 is a schematic of exemplary components of the vitrectomy probe system 110. The probe system 110 includes the vitrectomy probe 112, a pneumatic pressure source 120, a probe driver shown as an adjustable directional on-off pneumatic driver 122, a muffler 124, and a controller 126. In an embodiment, the controller 126 may be a processor that includes one or more processing cores capable of performing parallel or sequential operations. Alternatively, the controller 126 may be a dedicated piece of hardware such as an application specific integrated circuit (ASIC), to name just a few examples. The source 120, the driver 122, the muffler 124, and the probe 112 are in fluid communication with each other along lines representing flow paths or flow lines. The controller 126 is in electrical communication with the driver 122. In an embodiment, the controller 126 controls operation of both the driver 122 and various aspects of the probe 112, including the frequency of oscillation by way of the actuator as well as a flow rate of fluid to/from the surgical site.

Figure 3:
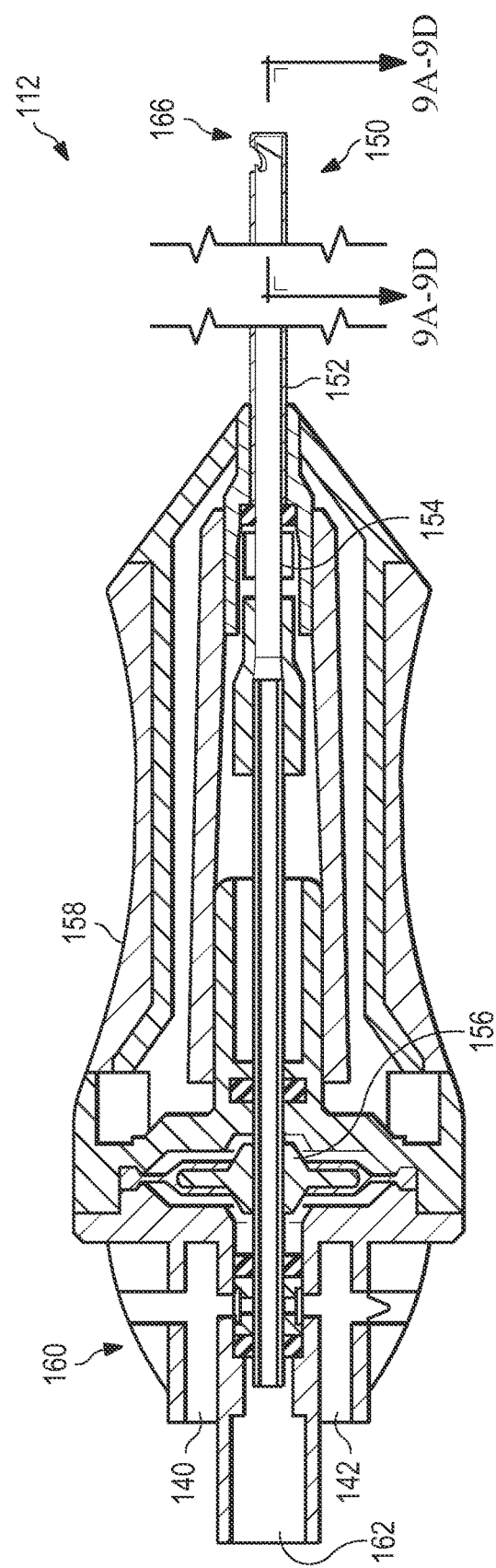
FIG. 3 is an illustration of an exemplary vitrectomy probe in cross-section operable in accordance with the principles and teachings described herein.

FIG. 3 shows a partial cross-sectional illustration of an exemplary vitrectomy probe, for example the vitrectomy probe 112 introduced in FIGS. 1 and 2. In this example, the vitrectomy probe 112 is a pneumatically driven probe that operates by receiving pneumatic pressure alternating through first and second ports 140 and 142. The probe 112 includes as its basic components a cutter 150 comprising an outer cutting tube 152, an inner cutting tube 154 shown in a non-sectional side view, and a probe actuator or motor shown here as a reciprocating air driven diaphragm 156, all partially encased by a housing 158. The housing 158 includes an end piece 160 at the probe proximal end with the first and second air supply ports 140, 142 and one suction port 162 to provide aspiration of materials from the cutter 150.

In an embodiment, the vitrectomy probe system's pneumatic driver 122 (FIG. 2) may be a standard four-way on-off valve. The pneumatic driver 122 may have a solenoid that operates to move the driver to one of the two on-off positions depicted in the example of FIG. 2. Here, the pneumatic driver 122 is in a position to provide pneumatic pressure to the first port 140 (FIG. 3), and to vent pneumatic pressure from the second port 142 (FIG. 3). In this position, pneumatic pressure may pass from the pressure source 120, through the on-off pneumatic driver 122, and to the first port 140 where the pneumatic pressure provides pneumatic power to the vitrectomy probe 112. At the same time, pneumatic pressure at the second port 142 may pass through the on-off pneumatic driver 122 to the muffler 124 where it is exhausted, for example, to the atmosphere. In the other position, the on-off pneumatic driver 122 allows pneumatic pressure to pass from the pressure source 120 to the second port 142, where the pneumatic pressure provides pneumatic power to the vitrectomy probe 112. At the same time, pneumatic pressure at the first port 140 can vent through the on-off pneumatic driver 122 to the muffler 124 where it is exhausted to the atmosphere. The on-off pneumatic driver may be configured to receive operating signals from the controller 126.

In operation, pneumatic pressure is directed alternately from the source 120 to the first and second ports 140, 142 to operate the vitrectomy probe 112. The on-off pneumatic driver 122 alternates between its two positions very rapidly to alternatingly provide pneumatic pressure to the first and second ports 140, 142. Although shown with a single pneumatic driver 122, other embodiments include two pneumatic drivers, one associated with each of the two ports 140, 142. These embodiments operate similar to the manner described, with the drivers being configured to independently receive operating signals from the controller 126 (FIG. 2). Yet other arrangements are contemplated.

Figure 8:
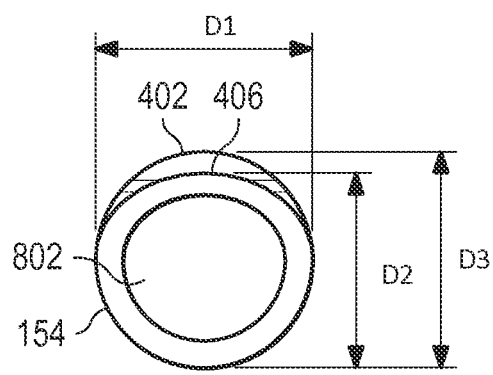
FIG. 8 is an illustration of an inner cutting tube in cross-section consistent with the principles and teachings described herein.

Returning to FIG. 3, the cutter 150 extends from the housing 158 and includes a distal end 166, shown in FIG. 4 in greater detail below. The outer cutting tube 152 and the inner cutting tube 154 may both be cylindrical tubes with a hollow bore. The inner cutting tube 154 may additionally have an open end, such as depicted in FIG. 8 as a distal port 802.

Generally, the inner cutting tube 154 oscillates within the outer cutting tube 152 in response to the probe actuator. In an embodiment, the inner cutting tube 154 is driven by air pressure directed on opposing sides of the diaphragm 156. In one example of operation, if air pressure is increased at the first port 140, the diaphragm 156 will move distally, displacing the inner cutting tube 154 relative to the outer cutting tube 152, thereby moving a first cutting edge on a distal end of the inner cutting tube 154 in the distal direction and cutting tissue. This cuts any vitreous material which may have been aspirated into a tissue-receiving outer port of the outer cutting tube 152. The vitreous may be aspirated away at a distal end of the inner cutting tube 154, such as distal port 802 of FIG. 8 discussed below in more detail. Venting the pressure at the first port 140 and increasing the pressure at the second port 142 moves the diaphragm 156 proximally, moving a second cutting edge facing a proximal direction near the distal end of the inner cutting tube 154 in the proximal direction, cutting any vitreous material which may have entered the ports of the inner cutting tube 154 and outer cutting tube 152 while at least partially aligned.

In alternative embodiments, the probe actuator may include a piston motor in place of a diaphragm. In this type of embodiment, the cutter 150 is arranged so that movement of the piston also moves the inner cutting tube 154 of the cutter 150. Yet other embodiments include other types of pneumatic or electric motors that drive the inner cutting tube 154, as will be recognized by those skilled in the relevant art(s).

Figure 4:
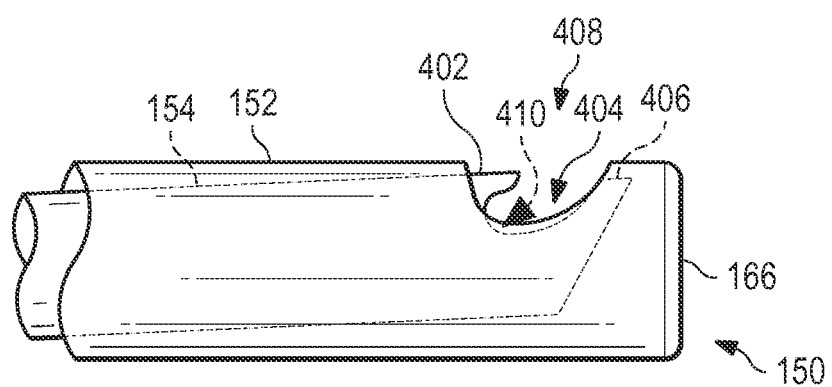
FIG. 4 is an illustration of an exemplary distal end of the vitrectomy probe in partial cross-section consistent with the principles and teachings described herein.

FIG. 4 illustrates an exemplary distal end of the vitrectomy probe 112. FIG. 4 illustrates in more detail the cutter 150 of FIG. 3 showing the outer cutting tube 152 and showing the inner cutting tube 154 in place in the outer cutting tube 152. The cutter 150 includes the inner cutting tube 154 and the outer cutting tube 152. The inner cutting tube 154 fits within the outer cutting tube 152 in a coaxial manner, and the inner cutting tube 154 is axially moveable relative to the outer cutting tube.

The outer cutting tube 152 has a closed end at the distal end 166 and an outer port 408 that may receive various material, such as tissue. In an embodiment, the tissue may be ophthalmic tissue such as vitreous and/or membrane. The outer port 408 has a distal portion, nearest the distal end 166, and a proximate portion. Each of the distal and proximate portions of the outer port 408 may include a cutting edge.

Figure 5:
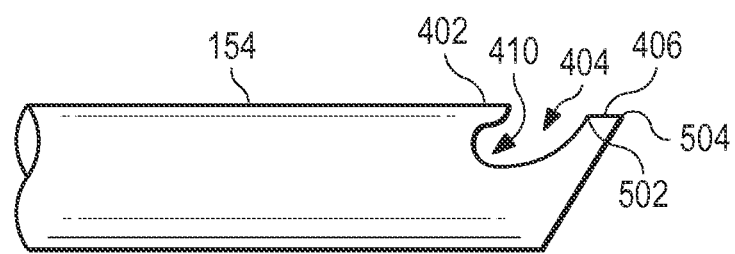
FIG. 5 is an illustration of an exemplary inner cutting tube consistent with the principles and teachings described herein.

FIG. 5 illustrates a distal portion of the inner cutting tube 154 specifically. The inner cutting tube 154 may have an open end at the distal end 166, such as distal port 802 (FIG. 8), and an inner port 404 to similarly receive material such as tissue. The inner port 404 has a distal side 502 that forms the proximate side of tip 406. Tip 406 also has a distal side 504 facing the distal end 166 of the cutter 150. The distal and proximate sides 504, 502 of the tip 406 may include cutting edges which, when moving with respect to the cutting edges on the outer port 408, cooperate to cut material such as tissue as will be described further below.

In an embodiment, the tip 406 may be crimped slightly, such that a horizontal diameter D1 of the tip 406 (the diameter that extends in a direction perpendicular from the direction towards the inner port 404) is greater than a vertical diameter D2 of the tip 406 (the diameter of the tip 406 that extends radially towards the inner port 404). This is demonstrated in FIG. 8, which illustrates the inner cutting tube 154 in cross-section perpendicular to the longitudinal axis of the inner cutting tube 154. The crimp in the tip 406 illustrated in FIGS. 4 and 8 imparts a unique tubular cross section to the inner cutting tube 154, such as a substantially oval cross section, in contrast to the rest of the inner cutting tube 154 that is approximately round.

In embodiments where the tip 406 of the inner cutting tube 154 has been slightly bent to provide bias toward the outer port 408, this different cross section at the tip 406 provides better matched shearing edges between the inner cutting tube 154 and the outer cutting tube 152. This better match facilitates smooth, progressive shearing of vitreous/membranes and reduces wear to the vitrectomy probe 112 over time. This is due at least in part to the substantially oval cross section at the tip 406 distributing the sliding wear at the tip 406 over a greater surface area that comes in contact with the inner surface of the distal end of the outer cutting tube 152. The substantially oval cross section of the tip 406 also decreases the size of the annular space between the tip 406 and the inner surface of the distal end of the outer cutting tube 152, which may decrease the potential for vitreous incarceration and vitreoretinal traction.

Returning to FIG. 5, the inner port 404 of inner cutting tube 154 has a proximate portion where guiding surface 402 is located. A side lobe 410 may be located on each side of the guiding surface 402 as contours along the periphery of the inner port 404. The side lobes 410, together, serve to define the guiding surface 402 as a protrusion in the distal direction from the otherwise generally uniform shape of the inner port 404 into the space of the inner port 404. The guiding surface 402 provides an additional surface which may slidably bear on an inner surface of the outer cutting tube 152 as the inner cutting tube 154 axially moves in the distal and proximal directions during operation.

As a result, in embodiments where the inner cutting tube 154 has been bent to provide a flexural side load, the guiding surface 402 remains in contact with the inner surface of the outer cutting tube 152 while the inner cutting tube 154 axially moves in the distal direction. This contact between the guiding surface 402 and the inner surface of the outer cutting tube 152 may prevent the inner cutting tube 154 from protruding too far out of the outer port 408, thereby decreasing the chance of tortuous or impeded cutter motion and reducing wear on the vitrectomy probe 112. The guiding surface 402 may be formed from the rest of the inner cutting tube 154. Alternatively, the guiding surface may be separately formed and secured in place at a proximal side of the inner port 404 using welding, brazing, cements, adhesives, friction fits, or other methods.

The side lobes 410 extend the surface area of the inner port 404, thereby allowing more fluid flow via the inner port 404 than would be available to a port with a conventional contour (e.g., without side lobes) in the inner cutting tube 154. In an embodiment, addition of the side lobes 410 to the vitrectomy probe 112 in embodiments of the present disclosure enables operation of the vitrectomy probe 112 at reduced vacuum settings while still providing equivalent vitreous flow and reduced traction transmitted to the retina relative to conventional vitrectomy probes. In an embodiment, the length of each side lobe 410 along the longitudinal axis of the inner cutting tube 154 is less than a width of the inner port 404 between the tip 406 and the proximal portion where the guiding surface 402 is located. In an alternative embodiment, the length of each side lobe 410 along the longitudinal axis of the inner cutting tube 154 is greater than a width of the inner port 404 between the tip 406 and the proximal portion where the guiding surface 402 is located.

The size of the side lobes 410 impacts how much additional fluid flow is possible above and beyond what is already available were the inner port 404 shaped in a conventional configuration, e.g. in a round or oval shape. This is because the vitreous humor, as well as tractional and vascular membranes that are commonly removed by surgical use of vitrectomy probes, are non-homogenous, non-Newtonian substances that tend to resist flow through small orifices and lumens such as those in conventional vitrectomy probes. Further, balanced saline solution—which is commonly used as an adjunct during vitreoretinal surgery—is a low viscosity Newtonian fluid that is much more able to flow through smaller passages. As a result, aspiration flow in cutter ports of conventional vitrectomy probes may result in a disproportionately high amount of balanced saline solution instead of vitreous/membranes. The larger inner port size afforded by the side lobes 410 in embodiments of the present disclosure facilitates the more efficient removal of vitreous/membranes without excessive flow of balanced saline solution.

Figure 6:
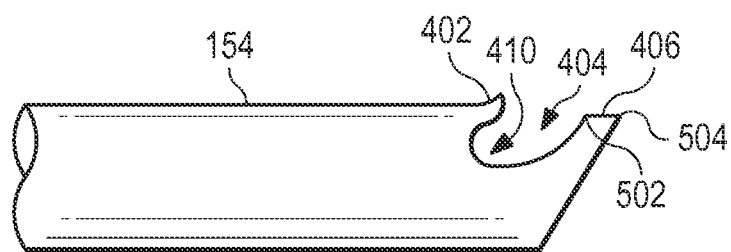
FIG. 6 is an illustration of an exemplary inner cutting tube consistent with the principles and teachings described herein.

FIG. 6 illustrates an alternative embodiment to that of FIG. 5 of the inner cutting tube 154. In the embodiment described in FIG. 5 above, the vertical diameter of the inner cutting tube 154 at the base of the guiding surface 402 is approximately the same as the vertical diameter of the inner cutting tube 154 at the edge of the guiding surface 402 (the edge that is proximate to, and partially defines the contour of, the inner port 404). In FIG. 6, the guiding surface 402 is flared out in a radial direction away from the longitudinal axis of the inner cutting tube 154. As a result, the vertical diameter of the inner cutting tube 154 at the edge of the guiding surface 402 proximate to the inner port 404 is greater than the vertical diameter of the inner cutting tube 154 at the base of the guiding surface 402. Both diameters of the guiding surface 402 are greater than the vertical diameter D2 (FIG. 8) of the tip 406, as was the case in FIG. 5 above.

The flare of the guiding surface 402 in FIG. 6 may be sized in such a manner as to increase the distance the tip 406 would have to traverse while in the area of the outer port 408 to result in protrusion too far outside of the diameter of the outer cutting tube 152 while the guiding surface 402 is slidably bearing on an inner surface of the outer cutting tube 152 at a proximal side of the outer port 408. The contact between the flared guiding surface 402 of FIG. 6 may further reduce the possibility of the inner cutting tube 154, the tip 406 specifically, from protruding too far out of the outer port 408 of the outer cutting tube 152 during axial motion of the inner cutting tube 154.

Figure 7:
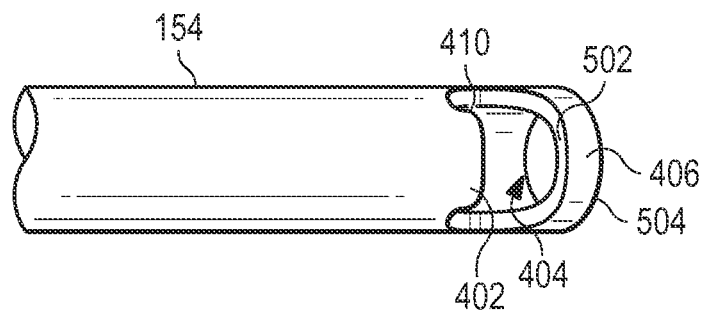
FIG. 7 is an illustration of a top view of an exemplary inner cutting tube consistent with the principles and teachings described herein.

FIG. 7 is an illustration of a top view of an exemplary inner cutting tube, such as the inner cutting tube 154. As can be seen, there is a side lobe 410 at each side of the guiding surface 402. The guiding surface 402 may be a protrusion into the inner port 404 that extends from the proximal side of the inner port 404 toward the distal end 166.

As discussed above with respect to FIG. 5, each of the distal side 504 and proximal side 502 of the tip 406 may include cutting edges. For purposes of discussion for FIG. 7, distal side 504 will be referred to as cutting edge 504 located at the distal side of the tip 406, and proximal side 502 will be referred to as cutting edge 502 located at the proximal side of the tip 406. Each of the cutting edges 502 and 504 may be ovally shaped cutting blades having an outer diameter along an upper circumference of the part of the inner cutting tube 154 where the inner port 404 is located that substantially matches the inner diameter of the outer cutting tube 152. As such, it is configured to also slide within the bore of the outer cutting tube 152. In some embodiments, the cutting edges 502 and 504 may be tapered or sharpened on their outer diameters in order to cleanly cut vitreous, for example into small segments for easy aspiration.

The proximate and distal portions of the outer port 408 may each also include a cutting edge. For example, a cutting edge on the distal portion of the outer port 408 may cooperate with the cutting edge 504 to perform shearing of vitreous or other tissue while the inner cutting tube 154 moves axially in the distal direction. Further, a cutting edge on the proximal portion of the outer port 408 may cooperate with the cutting edge 502 to perform shearing of vitreous or other tissue while the inner cutting tube 154 moves axially in the proximal direction.

FIG. 8 illustrates an exemplary inner cutting tube in cross-section and an exemplary distal end of the vitrectomy probe 112, respectively. In an embodiment, FIG. 8 illustrates the inner cutting tube 154 and the outer cutting tube 152. In particular, FIG. 8 illustrates the tip 406 of the inner cutting tube 154 having a crimp, such as one which imparts a substantially oval cross section, causing the tip 406 to have the vertical diameter D2 which is less than a vertical diameter D3 of the inner cutting tube 154 at the guiding surface 402. The resulting unique tubular cross section at the tip 406 provides better matched shearing edges, such as at least between the cutting edge 504 and the cutting edge on the distal portion of the outer port 408 and the cutting edge 502 and the cutting edge on the proximal portion of the outer port 408.

An inner bore of the inner cutting tube 154, depicted in FIG. 8 as distal port 802, may be in fluid communication with an aspiration line (not shown) that connects to a vacuum pressure that pulls tissue into outer port 408 when the inner cutting tube 154 is located away (in a proximal direction) from the outer port 408. The inner cutting tube 154 moves within the outer cutting tube 152 in a cyclic motion to drive the cutting edge 504 to cut tissue that is pulled into the outer port 408 by the aspiration system. The ophthalmic tissue received by the outer port 408 may be vitreous, membranes, or other tissue.

Figure 9A:
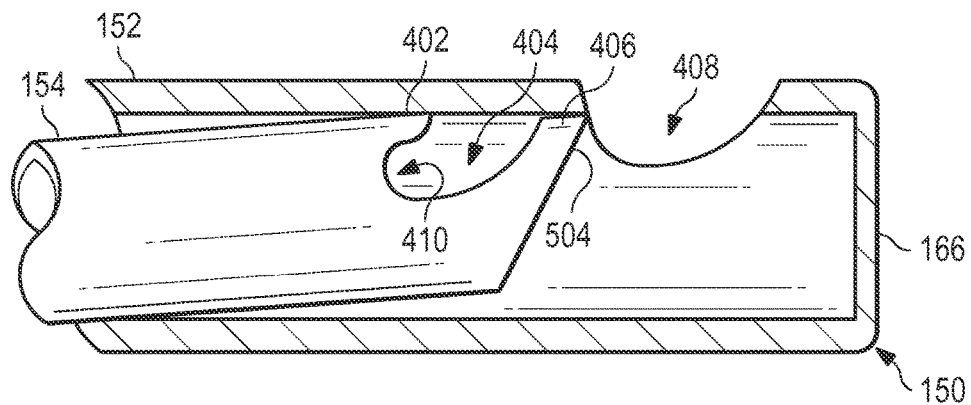
FIGS. 9A-9D are illustrations showing the inner and outer cutting tubes in partial cross-section and in different positions during a cutting cycle.

FIGS. 9A-9D show a cutting cycle of the vitrectomy cutter 150. FIG. 9A represents the portion of a cutting cycle when the inner cutting tube 154 is in the proximal (or "open") position. In this position, vacuum pressure in the inner cutting tube 154 (e.g., via the distal port 802 of FIG. 8) pulls tissue into the outer port 408 of the outer cutting tube 152.

Figure 9B:
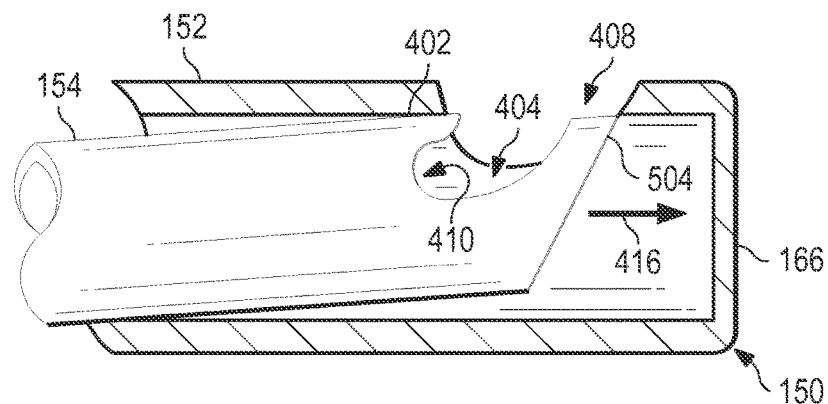

As shown in FIG. 9B, inner cutting tube 154, including the cutting edge 504 on the tip 406, travels distally toward distal end 166 of the outer cutting tube 152 in a distal motion 416. As it moves, the cutting edge 504 cuts vitreous tissue that has entered the outer port 408, severing the tissue within the bore of the outer cutting tube 152. The severed tissue is pulled through an inner bore, such as the distal port 802 (FIG. 8), of the inner cutting tube 154 by the aspiration system. At the same time, the vacuum pressure from the aspiration system continues to pull tissue into the outer port 408.

As the tip 406 of the inner cutting tube 154 traverses the open area of the outer port 408, the guiding surface 402 slidably bears on an inner surface of the outer cutting tube 152 at a proximal side of the outer port 408. In this manner, the unique contour of the guiding surface 402 may guide the inner cutting tube 154 so that the tip 406 does not protrude too far beyond a diameter of the outer cutting tube 152. Further, the unique tubular cross section of the tip 406 may cause the cutting edge 504 to more closely align to the inner diameter of the outer cutting tube 152, increasing the surface area that comes into contact between the two surfaces resulting in smooth, progressive shearing of tissue.

Figure 9C:
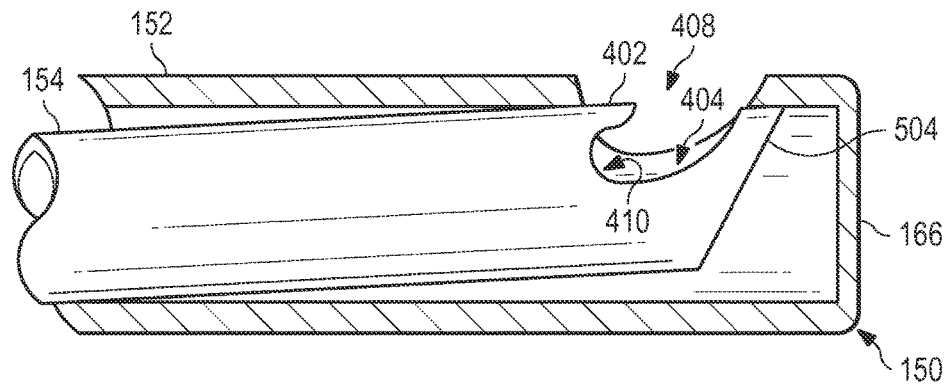

The inner cutting tube 154 moves distally until the cutting edge 504 is beyond the outer port 408, as shown in FIG. 9C. In an embodiment, the tip 406 may become substantially flush with the distal end 166. Alternatively, the tip 406 may leave a gap between the cutting edge 504 and the distal end 166. In either embodiment, the inner port 404 is at least partially aligned with the outer port 408 while the inner cutting tube 154 is in the distal (or "closed") position. As a result, tissue enters through the outer port 408 and into the inner port 404 while at least partially aligned with the outer port 408.

Figure 9D:
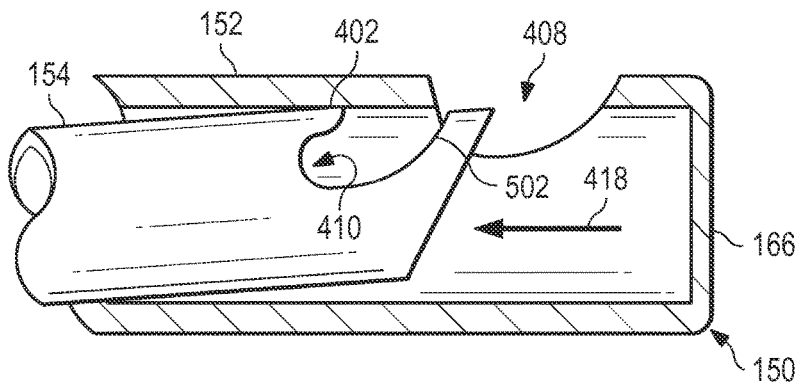

As shown in FIG. 9D, the inner cutting tube 154 then moves in the proximal direction in a proximal motion 418. This draws the tip 406 in the proximal direction. As the tip 406 moves in the proximal direction, the cutting edge 502 cuts tissue that has entered the inner port 404, severing the tissue within the inner bore of the inner cutting tube 154. The severed tissue is pulled through the inner bore of the inner cutting tube 154 by the aspiration system, and the inner cutting tube 154 returns to the position shown in FIG. 9A.

The side lobes 410 of the inner cutting tube 154 increase the size along the periphery of the inner port 404, thereby decreasing resistance to tissue (such as vitreous) flow when the guiding surface 402 is aligned at least partially with the outer port 408. This facilitates the more efficient removal of vitreous/membranes without excessive flow of balanced saline solution. Further, during the proximal motion 418 the guiding surface 402 slidably bears on the inner surface of the outer cutting tube 152 at the proximal side of the outer port 408, again guiding the inner cutting tube 154 while the tip 406 traverses the gap of the outer port 408 in the proximal direction.

Because the cutting action occurs as the inner cutting tube 154 moves in both the proximal and the distal directions, the cutting edges perform a dual-action cutting cycle. This may double the cut rate of the vitrectomy probe 112. For example, while still operating the motor of the vitrectomy probe 112 at 10000 cycles/min., the effective cut rate is 20000 cycles/min since each cycle provides both an anterior cut and a posterior cut.

Figure 10:
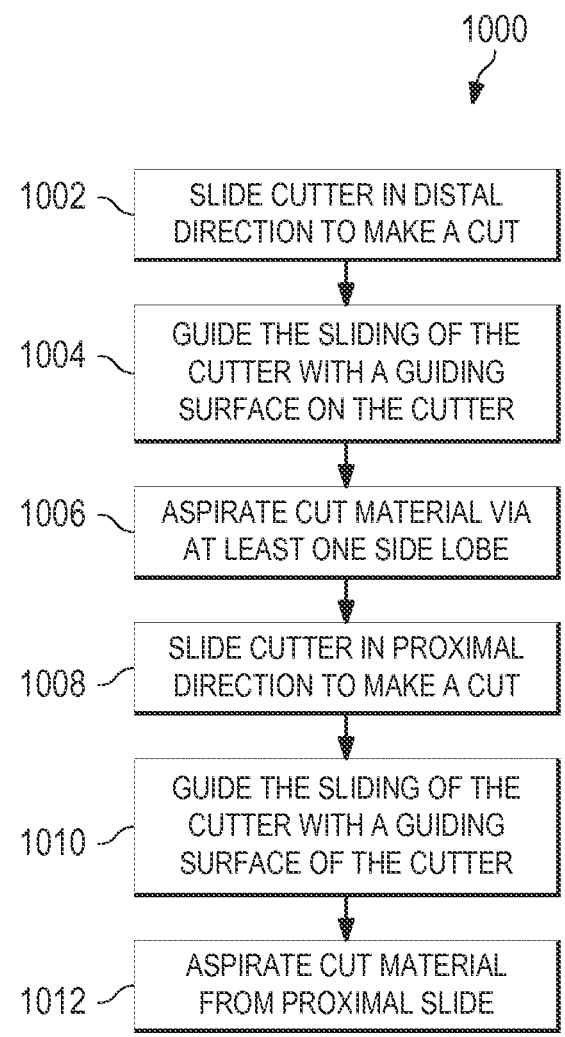
FIG. 10 is an illustration of an exemplary method of operation of the vitrectomy probe consistent with the principles and teachings described herein.

FIG. 10 is an illustration of an exemplary method 1000 of operation a vitrectomy probe. In an embodiment, method 1000 illustrates a method of operation of the vitrectomy probe 112 operating as part of the vitrectomy probe system 110 discussed above. In operation, the distal end 166 of the vitrectomy cutter 150 may be introduced into an eye of a patient to be treated for an ocular condition. A vacuum may be used to draw fluid and tissue, such as vitreous, into the outer port 408 during operation.

At 1002, the vitrectomy probe 112 causes the inner cutting tube 154 to slide in a distal direction, such as shown by the distal motion 416 in FIG. 9B. As the cutting edge 504 at the tip 406 of the inner cutting tube 154 moves distally, the cutting edge 504 cuts tissue that has entered the outer port 408 of the outer cutting tube 152. The inner cutting tube 154 may be bent near its distal end to provide a flexural side load, causing the guiding surface 402 to be engaged with an inner surface of the outer cutting tube 152. In this angled position, the tip 406 is disposed in a position that is a suitable distance removed from, or is disposed to also engage with, the inner surface of the outer cutting tube 152 in order to cut fibrils or tissue without creating damaging traction on the retina.

At 1004, the guiding surface 402 of the inner cutting tube 154 guides the distal sliding motion of the inner cutting tube 154 as the tip 406 of the inner cutting tube 154 traverses the gap of the outer port 408 in the distal direction. The guiding surface 402 guides the sliding motion, for example, by slidably bearing on an inner surface of the outer cutting tube 152 at a proximal side of the outer port 408. The guiding motion assists in preventing the tip 406 from protruding too far beyond a diameter of the outer cutting tube 152 as a result of the bend in the inner cutting tube 154.

At 1006, the vitrectomy probe 112 aspirates any cut tissue from the distal end of the inner cutting tube 154, for example via the distal port 802. The aspiration may be via the suction port 162 that connects the vitrectomy probe 112 to an aspiration system on the base housing 102. This may occur, for example, when the inner cutting tube 154 has been fully extended in the distal direction, in the "closed" position such that the inner port 404 and the outer port 408 are at least partially aligned.

At 1008, the vitrectomy probe 112 causes the inner cutting tube 154 to slide in the proximal direction, such as shown by the proximal motion 418 in FIG. 9D. As the cutting edge 502 at the proximal side of the tip 406 moves proximally, the cutting edge 502 cuts tissue that has entered the inner port 404 and the outer port 408 while they are aligned, either substantially or partially.

At 1010, the guiding surface 402 guides the proximal sliding motion of the inner cutting tube 154 as the tip 406 traverses the gap of the outer port 408 in the proximal direction. The guiding surface 402 guides the sliding motion, for example, by slidably bearing on an inner surface of the outer cutting tube 152 at a proximal side of the outer port 408.

At 1012, the vitrectomy probe 112 aspirates any cut tissue and/or fluids from the area of the inner port 404. The aspiration may again be via the suction port 162. At least some of the cut tissue and/or fluids is aspirated at step 1012 via one or both of the side lobes 410, since the side lobes 410 of the inner cutting tube 154 increase the size along the periphery of the inner port 404 from which tissue may enter the inner bore of the inner cutting tube 154. This facilitates the more efficient removal of vitreous/membranes without excessive flow of balanced saline solution. While described as a discrete aspiration step, it is worth noting that the aspiration system may draw a constant or continuous vacuum pressure at the suction port 162 and the bore (lumen) of the inner cutting tube 154.

1002 through 1012 may continue throughout the duration of operation of the vitrectomy probe 112, resulting in a dual-action cutting cycle of the vitrectomy probe 112 with improved fluid flow and reduced sliding wear on the vitrectomy probe 112 over time. This may result in a longer lasting vitrectomy probe, a smoother cutting cycle, and greater cut rates while decreasing risks of traction on the retina.

The systems, devices, and method described herein may improve surgical outcome by increasing cut rates and aspiration rates while reducing wear to enable increased probe reliability and longevity.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A vitrectomy probe, comprising:
    a hand-graspable body;
    an outer tube extending from the hand-graspable body and sized to penetrate an eye of a patient during an ocular surgery, the outer tube having a closed distal end and a first port sized to receive vitreous of the eye; and
    an inner tube disposed at least partially within the outer tube, the inner tube comprising a second port selectively alignable with a portion of the first port in a manner that allows fluid to flow through the first port and into the second port, the second port having a proximal edge and a distal edge, the inner tube also comprising a distal tip forming a first cutting edge facing in a distal direction, the distal edge of the second port forming a second cutting edge facing in a proximal direction, the inner tube having a first diameter at a proximal end of the second port and having a second diameter at the distal tip, the first diameter being greater than the second diameter;
    wherein the first cutting edge is configured to cut tissue that enters the first port of the outer tube as the inner tube slides in a distal direction; and
    wherein the second cutting edge is configured to cut tissue that enters the second port of the inner tube as the inner tube slides in the proximal direction;
    wherein the second port further comprises:
       a guiding surface at the proximal edge projecting in the distal direction to form a distally extending portion, the guiding surface being arranged to slidably bear on an internal surface of the outer tube while the inner tube moves relative to the outer tube, the first diameter comprising a diameter of the inner tube at the guiding surface.

2. The vitrectomy probe of claim 1, wherein the second port further comprises:
    a first side lobe and a second side lobe each at opposite sides of the guiding surface along a circumference of the inner tube, the first and second side lobes configured to enhance fluid flow through the second port when the guiding surface is at least partially aligned with the first port.

3. The vitrectomy probe of claim 2, wherein the guiding surface radially extends in a direction perpendicular to a longitudinal axis of the inner tube such that a base of the guiding surface has the first diameter and an edge of the guiding surface facing into the second port has a third diameter, the third diameter being greater than the first diameter.

4. The vitrectomy probe of claim 2, wherein the first side lobe and the second side lobe each have a length in the proximal direction that is less than a distance between the proximal and distal edges of the second port.

5. The vitrectomy probe of claim 2, wherein the first side lobe and the second side lobe each have a length in the proximal direction that is greater than or equal to a distance between the proximal and distal edges of the second port.

6. The vitrectomy probe of claim 1, wherein:
    the guiding surface is configured to provide a guide for the inner tube disposed within the outer tube as the first cutting edge moves in a distal direction across the first port to cut tissue aspirated into the first port, and
    the second cutting edge is configured to cut tissue aspirated into the first port as the second cutting edge moves in the proximal direction across the first port.

7. A vitrectomy probe, comprising:
    a hand-graspable body;
    an outer tube extending from the hand-graspable body and sized to penetrate an eye of a patient during an ocular surgery, the outer tube having a closed distal end and a first port sized to receive vitreous of the eye; and
    an inner tube within the outer tube and comprising a second port having a proximal end and a distal end along a side of a circumference of the inner tube near a distal end of inner tube, the second port comprising a guiding surface at the proximal end extending in a distal direction, a first side lobe, and a second side lobe, each of the first and second side lobes formed in part by the guiding surface and disposed at opposite sides of the guiding surface along the circumference of the inner tube to enhance fluid flow through the second port when the guiding surface is at least partially aligned with the first port, wherein the distally extending guiding surface is a guide for the inner tube disposed within the outer tube as the inner tube oscillates in the outer tube.

8. The vitrectomy probe of claim 7, wherein the inner tube further comprises:
   a tip at a distal end of the inner tube;
   a first cutting edge facing in a distal direction at a distal end of the tip; and
   a second cutting edge facing in a proximal direction at a proximal end of the tip, the second cutting edge further defining the distal end of the second port.

9. The vitrectomy probe of claim 8, wherein:
   a first diameter of the inner tube at the proximal end of the second port is greater than a second diameter of the inner tube at the tip.

10. The vitrectomy probe of claim 9, wherein the guiding surface radially extends from the inner tube such that a base of the guiding surface has the first diameter and an edge of the guiding surface facing into the second port has a third diameter, the third diameter being greater than the first diameter.

11. The vitrectomy probe of claim 9, wherein the tip comprises a crimp imparting an ovalized tubular cross-section profile to the tip.

12. The vitrectomy probe of claim 11, wherein the ovalized tubular cross-section profile of the tip is configured to substantially align with a contour of an inner surface of the outer tube.

13. The vitrectomy probe of claim 7, wherein the first side lobe and the second side lobe each have a length in a proximal direction that is greater than or equal to a distance between the proximal and distal ends of the second port.

* * * * *